United States Patent
Nishimura et al.

(10) Patent No.: US 11,523,977 B2
(45) Date of Patent: Dec. 13, 2022

(54) MULTI-AGENT TYPE HAIR TREATMENT AGENT

(71) Applicant: KAO CORPORATION, Tokyo (JP)

(72) Inventors: Azusa Nishimura, Chiba (JP); Haruna Suzuki, Adachi-ku (JP); Shinobu Nagase, Nakano-ku (JP)

(73) Assignee: KAO CORPORATION, Tokyo (JP)

( * ) Notice: Subject to any disclaimer, the term of this patent is extended or adjusted under 35 U.S.C. 154(b) by 403 days.

(21) Appl. No.: 16/613,504

(22) PCT Filed: May 14, 2018

(86) PCT No.: PCT/JP2018/018539
§ 371 (c)(1),
(2) Date: Nov. 14, 2019

(87) PCT Pub. No.: WO2018/212129
PCT Pub. Date: Nov. 22, 2018

(65) Prior Publication Data
US 2021/0154111 A1 May 27, 2021

(30) Foreign Application Priority Data
May 17, 2017 (JP) ................................ 2017-097869

(51) Int. Cl.
*A61Q 5/02* (2006.01)
*A61K 8/368* (2006.01)
*A61K 8/365* (2006.01)
*A61K 8/41* (2006.01)
*A61K 8/86* (2006.01)
*A61Q 5/06* (2006.01)
*A61Q 5/12* (2006.01)

(52) U.S. Cl.
CPC .............. *A61K 8/368* (2013.01); *A61K 8/365* (2013.01); *A61K 8/41* (2013.01); *A61K 8/86* (2013.01); *A61Q 5/02* (2013.01); *A61Q 5/06* (2013.01); *A61Q 5/12* (2013.01); *A61K 2800/5424* (2013.01); *A61K 2800/5426* (2013.01)

(58) Field of Classification Search
CPC ... A61Q 5/02; A61Q 5/12; A61Q 5/06; A61K 2800/5426; A61K 8/365; A61K 8/368; A61K 2800/5424
USPC ....................................................... 424/70.1
See application file for complete search history.

(56) References Cited

U.S. PATENT DOCUMENTS

| | | |
|---|---|---|
| 5,683,685 A | 11/1997 | Hirano et al. |
| 2011/0150804 A1 | 6/2011 | Nojiri et al. |
| 2016/0228342 A1 | 8/2016 | Rose |
| 2019/0038532 A1 | 2/2019 | Niwano et al. |
| 2019/0388324 A1 | 12/2019 | Nagasaki et al. |

FOREIGN PATENT DOCUMENTS

| | | |
|---|---|---|
| EP | 0 629 395 B1 | 12/1994 |
| EP | 0 662 314 A1 | 7/1995 |
| JP | 6-298625 A | 10/1994 |
| JP | 6-305942 A | 11/1994 |
| JP | 8-198732 A | 8/1996 |
| JP | 2001-31531 A | 2/2001 |
| JP | 2006-282613 A * | 10/2006 |
| JP | 2010-65022 A | 3/2010 |
| JP | 2015-120660 A | 7/2015 |
| JP | 2016-185938 A | 10/2016 |
| JP | 2016-190806 A | 11/2016 |
| JP | 2017-19759 A | 1/2017 |
| JP | 2017-25004 A | 2/2017 |
| JP | 2017-119689 A | 7/2017 |
| JP | 2018-184350 A | 11/2018 |
| JP | 2018-199633 A | 12/2018 |
| WO | WO 2015/036051 A1 | 3/2015 |
| WO | WO 2018/142484 A1 | 8/2018 |

OTHER PUBLICATIONS

English transaltion (Mar. 19, 2022) of JP2006-282613 A.*
International Search Report dated Jul. 17, 2018 in PCT/JP2018/018539 filed on May 14, 2018.
Extended European Search Report dated Dec. 3, 2020 in European Patent Application No. 18801281.9, 10 pages.
Database GNPD[Online]MITEL; Apr. 10, 2009, anonymous: "Shampoo & Conditioner Miniset", XP055752111, retrieved from www.gnpd.com, Database accession No. 1088681, 3 pages.
Database GNPD[Online]MITEL; Dec. 22, 2005, anonymous: "Haircare Range", XP055752116, retrieved from www.gnpd.com, Database accession No. 422899.

* cited by examiner

*Primary Examiner* — Eisa B Elhilo
(74) *Attorney, Agent, or Firm* — Oblon, McClelland, Maier & Neustadt, L.L.P.

(57) ABSTRACT

A multi-agent type hair treatment agent comprising a first composition containing component (A) and component (B); and a second composition containing component (C), wherein the weight ratio (H)/(C) of component (H) to component (C) in the second composition is less than 1. A hair treatment method comprising the steps of applying and rinsing the first composition to hair (i) and then applying the second composition to hair (ii).

Component (A): a carboxylic acid having an inorganic value of 230 or more and 450 or less and an organic value of 50 or more and 250 or less, or a salt of the carboxylic acid
Component (B): anionic surfactant
Component (C): an aromatic sulfonic acid having a molecular weight of 300 or less or a salt thereof
Component (H): cationic surfactant.

11 Claims, No Drawings

MULTI-AGENT TYPE HAIR TREATMENT AGENT

FIELD OF THE INVENTION

The present invention relates to a multi-agent type hair treatment agent and a hair treatment method.

BACKGROUND OF THE INVENTION

Hair-related problems often include difficulty in straightening curling and waviness, lack of setting, and undesirable hairstyle finishing. In order to solve these problems, it is common to use a hair styling agent (wax, mist, foam, etc.) or the like, that is, cleaving and re-forming hydrogen bonds within the hair, or adhering the hair to each other. However, this process is complicated and is not sufficient from the viewpoint of facilitating shaping. In addition, the application of the treatment agent to the hair surface is not effective from the viewpoint of deterioration of feel such as smoothness or the like. For this reason, various methods of enhancing the shapeability of hair by a simple method and simultaneously providing the hair with consistency and smoothness have been investigated.

Patent Document 1 describes a hair treatment composition containing glycylglycine and a specific carboxylic acid, or even a specific aromatic sulfonic acid, as a technique for facilitating and maintaining the style while preventing the sleepiness of the hair.

Patent Document 2 describes a keratin fiber treatment agent composed of two agents, a treatment agent A containing a specific aromatic compound and a treatment agent B containing a polyvalent metal salt, as a technique which can shape keratin fibers while imparting tension/stiffness, and keeps the shape of keratin fibers for a long period of time.

Patent Document 3 describes a hair treatment agent composition containing aromatic sulfonic acids, oxyacids, silicone derivatives, and specific organic solvents as a technique for imparting excellent settability and consistency only by application to hair.

(Patent Document 1) JP-A-2010-65022
(Patent Document 2) JP-A-6-305942
(Patent Document 3) JP-A-6-298625

SUMMARY OF THE INVENTION

The present invention provides a multi-agent type hair treatment agent comprising
a first composition containing component (A) and component (B); and
a second composition containing component (C),
wherein the weight ratio (H)/(C) of component (H) to component (C) in the second composition is less than 1.

Component (A): a carboxylic acid having an inorganic value of 230 or more and 450 or less and an organic value of 50 or more and 250 or less, or a salt of the carboxylic acid.

Component (B): anionic surfactant

Component (C): an aromatic sulfonic acid having a molecular weight of 300 or less or a salt thereof Component (H): cationic surfactant The present invention also provides a hair treatment method comprising the following steps (i) to (ii).

Step (i): applying and rinsing the first composition containing component (A) and component (B) to hair.

Step (ii): after step (i), applying to the hair a second composition containing component (C) and having a weight ratio (H)/(C) of component (H) to component (C) of less than 1.

DETAILED DESCRIPTION OF THE INVENTION

The shaping property for hair in the techniques described in Patent Documents 1 to 3 is evaluated by shaping the hair in a wet state with water and observing the persistence of shaping after drying. Thus, the shapeability in these techniques can be attributed to the cleavage and recombination of hydrogen bonds within the hair, i.e., the so-called water set, which occurs when the hair dries from a wet state with water. Therefore, the techniques described in Patent Documents 1 to 3 do not improve the shaping property of hair after being treated with a hair treatment agent and then "dried". In particular, the technique described in Patent Document 1 has an effect of making the hair less likely to be sleepy, and therefore, it can also be referred to as a technique of lowering the shaping property of the hair after drying.

The present invention has been made in view of such circumstances, and relates to a multi-agent type hair treatment agent and a hair treatment method capable of enhancing not only consistency when wet hair is dried, but also shaping property to hair after drying, and imparting smoothness to hair.

The present inventors found that the above requirements are achieved by constructing a multi-agent type hair treatment agent comprising a first composition containing a specific carboxylic acid and an anionic surfactant, and a second composition containing a specific aromatic sulfonic acid and the ratio of the cationic surfactant to the aromatic sulfonic acid is limited to a certain value or less, and by sequentially treating the hair with the first composition and the second composition.

According to the multi-agent type hair treatment agent and the hair treatment method of the present invention, not only the consistency when wet hair is dried but also the shaping property for hair after drying can be enhanced, and moreover, smoothness can be imparted to hair.

The multi-agent type hair treatment agent comprising the first composition and the second composition of the present invention can further be used with a third composition. A multi-agent type hair treatment agent comprising a first composition and a second composition, optionally a third composition, of the present invention is a treatment agent for use by applying the first composition, followed by the second composition, optionally followed by the third composition, to the hair without mixing prior to use.

[First Composition]

The first composition is a composition containing a carboxylic acid or a salt thereof having an inorganic value of from 230 or more to 450 or less and an organic value of from 50 or more to 250 or less as a component (A), and an anionic surfactant as a component (B).

<Component (A): A Carboxylic Acid Whose Inorganic and Organic Values are within a Specified Range, or a Salt of the Carboxylic Acid>

Component (A) is a carboxylic acid having an inorganic value of 230 or more to 450 or less and an organic value of 50 or more to 250 or less, or a salt of the carboxylic acid. The inorganic value and the organic value in the component (A) refer to the inorganic value and the organic value of the carboxylic acid. That is, in the case of a carboxylic acid salt, it means an inorganic value and an organic value for the free acid. From the viewpoint of improving setting of hair bundles after drying and from the viewpoint of improving shapeability to hair after drying, the inorganic value is preferably 240 or more, more preferably 250 or more, even more preferably 260 or more, even more preferably 265 or more, even more preferably 270 or more, even more preferably 280 or more, even more preferably 290 or more, and preferably 420 or less, even more preferably 400 or less, even more preferably 390 or less, and even more preferably 380 or less. The combination of the inorganic values is preferably 240 or more and 420 or less, more preferably 250 or more and 420 or less, still more preferably 260 or more and 420 or less, still more preferably 270 or more and 420 or less, still more preferably 270 or more and 400 or less, and still more preferably 280 or more and 380 or less. In addition, from the same viewpoint, the organic value is preferably 60 or more, more preferably 70 or more, more preferably 80 or more, and preferably 200 or less, more preferably 180 or less, still more preferably 160 or less, still more preferably 150 or less, and still more preferably 120 or less. The combination of the organic values is preferably 60 or more and 200 or less, more preferably 60 or more and 160 or less, and still more preferably 70 or more and 150 or less.

The inorganic value and the organic value are based on an organic conception diagram, and are calculated based on "Formulation Design with Organic Conception Diagram" (Yamori; Fragrance Journal, 1989(4); pages 29 to 38).

Examples of such carboxylic acids include carboxylic acids represented by the following general formula (1), malic acid, succinic acid, and lactic acid.

[1]

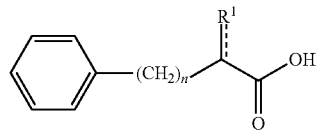
(1)

[wherein $R^1$ represents a hydrogen atom, an oxygen atom, or a hydroxy group, the dashed line represents a double bond when $R^1$ is an oxygen atom, n represents an integer of 0 or more and 3 or less, and a portion of the phenyl group and the methylene chain may be substituted with a hydroxy group.]

Examples of the carboxylic acid represented by the general formula (1) include mandelic acid, phenyllactic acid, and the like. Specific inorganic and organic values of these carboxylic acids are mandelic acid (265, 160), phenyllactic acid (265, 180), malic acid (400, 80), succinic acid (300, 80), and lactic acid (250, 60). The numerical values in parentheses indicate the inorganic value and the organic value, respectively.

As the component (A), succinic acid, malic acid, lactic acid, mandelic acid and salts thereof are preferable from the viewpoint of improving the setting of hair bundles after drying. Among these, succinic acid, malic acid, and their salts are more preferable from the viewpoints of setting of hair bundles after drying, stress relaxation rate of dry hair, and excellent shaping property when stress is applied to dry hair, and succinic acid and its salts are more preferable.

Salts of the above carboxylic acids include sodium salt, potassium salt, lithium salt, aluminum salt, ammonium salt, organic quaternary ammonium salt, arginine salt, and the like.

These carboxylic acids or salts thereof can be used alone or in combination of two or more kinds. The content of the component (A) in the first composition is preferably 0.1% by mass or more, more preferably 0.3% by mass or more, more preferably 0.5% by mass or more, still more preferably 0.8% by mass or more, and also preferably 5% by mass or less, more preferably 4% by mass or less, still more preferably 3.0% by mass or less, and still more preferably 2.5% by mass or less from the viewpoints of improving the setting of hair bundles after drying, stress relaxation rate of dry hair, and formability when stress is applied to dry hair.

<Component (B): Anionic Surfactant>

The anionic surfactant of component (B) is preferably a sulfuric acid, sulfonic acid, or carboxylic acid based surfactant, and examples thereof include alkyl sulfate, polyoxyalenekyl alkyl ether sulfate, polyoxyalkylene alkenyl ether sulfate, sulfosuccinic acid alkyl ester, sulfosuccinic acid alkylelenealkyl phenyl ether sulfate, alkanesulfonic acid salt, higher fatty acid salt, alkyl ether carboxylic acid, or a salt thereof. Among them, polyoxyalkylene alkyl ether sulfate and alkylsulfate are preferable, and further, those represented by the following general formula (2) or (3) are preferable.

[wherein $R^2$ represents an alkyl group or an alkenyl group having from 10 to 18 carbons, M represents an alkali metal, an alkaline earth metal, or ammonium, and m represents a number of from 1 to 30 of a weight-average.]

Among these, polyoxyethylene alkyl ether sulfates in which $R^2$ in the general formula (2) is an alkyl group having from 12 to 14 carbons, m is from 1 to 10 of a weight-average, and M is ammonium or sodium are preferable from the viewpoint of achieving both rapid foaming and good foam feeling.

The anionic surfactant of the component (B) can be used alone or in combination of two or more kinds, and the content of the component (B) in the first composition is preferably 1% by mass or more, more preferably 3% by mass or more, still more preferably 5% by mass or more, and preferably 30% by mass or less, more preferably 20% by mass or less, and still more preferably 15% by mass or less from the viewpoints of easy washing of hair and high washing power.

<Component (D): Cationic Polymer>

It is preferable that the first composition further contains a cationic polymer as the component (D) from the viewpoint of reducing the creep during washing of the hair and improving the smoothness of the hair bundle after drying.

Examples of the cationic polymer include a natural or semi-synthetic cationic polysaccharide, a synthetic polymer containing an amino group or an ammonium group in a side chain of a polymer chain, or a diallyl quaternary ammonium salt as a constituent unit.

Examples of cationic polysaccharides include cationized cellulose (e.g., Lion: Leogard G, Leogard GP, Dow Chemical Company: UCARE Polymer JR-125, UCARE JR-400, UCARE LR-400, UCARE Polymer 30M, UCARE Polymer LR-30M, Akzonobel: Celcoat H-100, Celcoat L-200, Kao: Poiz C-60H, Poiz C-80M, Poiz C-150L), cationized guar gum (e.g., Solvey: Jaguar C-13S, Jaguar C-17, DSP Gokyo Food & Chemical: Rhaball gum CG-M, Rhaball gum CG-M7, Rhaball gum CG-M8M), cationized taragum (e.g., Toho Chemical Industry: Catinal CTR-100, Catinal L-200), cationized locust bean gum (e.g., Toho Chemical Industry:

Catinal LB-100), cationized fenugreek gum (e.g., Toho Chemical Industry: Catinal CF-100), hydroxypropyl chitosan (e.g., Ichimaru Pharcos Co., Ltd: Chitofilmer HV-10), chitosan-dl-pyrolidone carboxylic acid (e.g., Union carbide Co., kytamer PC) and the like are exemplified.

Synthetic cationic polymers containing amino or ammonium groups in the side chains of the polymer include trialkylaminoalkyl (meth)acrylate, trialkylaminoalkyl (meth)acrylamide, (meth)acrylamide, vinyl amine, and the like; specific examples are polymers of methacryloyloxy-ethylenetrimonium chloride (INCI name: Polyquaternium-37, for example, BASF: Cosmedia Ultragel 300, SALCARE SC95, Sigma 3V: synthalen CR), (acrylic acid/methyl acrylate/3-methactylolaminopropyltrimethylammonium chloride) copolymer (INCI name: Polyquaternium-47, for example, Lubrizol: Merquat 2201), (acrylic acid/acrylamido/methylmethacrylamidopropyltrimethylammonium chloride) copolymer (INCI name: polyquaternium-53, for example, Lubrizol: Merquat 2003), (dimethylacrylamide/ ethyltrimonium methacrylate chloride) copolymers (e.g., BASF: Tinobis CD), (vinylamine/vinylalcohol) copolymers (e.g., Sekisui Specialty Chemical: SEVOL ULTALUX AD, Mitsubishi Chemical: Diafix C-601), etc.

Examples of synthetic cationic polymers containing diallyl quaternary ammonium salts as building blocks include polymers of diallyldimethylammonium chloride (INCI name: Polyquaternium-6, e.g., Lubrizol: Merquat 100), (dimethyldiallyammonium chloride/acrylamide)copolymers (INCI Polyquaternium-7, e.g., Lubrizol: Merquat 550, 740), (acrylic acid/diallyldimethylammonium Chloride) copolymers (INCI name: polyquaternium-22, e.g., Lubrizol: Merquat 280, 295), (acrylamide/acrylic acid/diallylammonium chloride) copolymer (INCI name: polyquaternium-39, for example, Lubrizol Corporation: Merquat Plus 3330, 3331).

Of these, natural or semisynthetic cationic polysaccharides are preferable, and cationized cellulose and cationized guar gum are more preferable. The cationic polymer of component (D) can be used alone or in combination of two or more. The content of the component (D) in the first composition is preferably 0.01% by mass or more, more preferably 0.05% by mass or more, more preferably 0.10% by mass or more, and preferably 5% by mass or less, more preferably 3% by mass or less, and still more preferably 1% by mass or less from the viewpoint of improving the smoothness of the hair bundle after drying.

<Component (E): Nonionic Surfactant>

The first composition preferably further contains a nonionic surfactant as component (E). Nonionic surfactants include polyoxyalkylene alkyl ethers, polyoxyalkylene alkenyl ethers, higher fatty acid sucrose esters, polyglycerol fatty acid esters, higher fatty acid mono- or diethanolamides, polyoxyethylene hardened castor oil, polyoxyethylene sorbitan fatty acid esters, alkyl saccharides, alkylamine oxides, alkyl amidoamine oxides, alkyl glyceryl ethers, alkenyl glyceryl ethers, and the like.

Among these, polyoxyalkylene alkyl ether, polyoxyalkylene alkenyl ether, alkylglyceryl ether, and alkenylglyceryl ether are preferable. The nonionic surfactant of component (E) can be used alone or in combination of two or more. The content of the component (E) in the first composition is preferably 0.01% by mass or more, more preferably 0.5% by mass or more, more preferably 1.0% by mass or more, and preferably 15% by mass or less, more preferably 10% by mass or less, and still more preferably 5% by mass or less from the viewpoint of obtaining high detergency and good foaming effect.

<Component (F): Amphoteric Surfactants>

The first composition preferably further contains a amphoteric surfactant as component (F). Examples of the amphoteric surfactant include a carbobetaine-based surfactant, an amidobetaine-based surfactant, a sulfobetaine-based surfactant, a hydroxysulfobetaine-based surfactant, an amidosulfobetaine-based surfactant, a phosphobetaine-based surfactant, and an imidazolinium-based surfactant having an alkyl group, an alkenyl group, or an acyl group, having from 8 Lo 24 carbon atoms, among which an amidobetaine-based surfactant and a hydroxysulfobetaine-based surfactant are preferable. Preferred amphoteric surfactants include laurate amidopropyl betaine, lauryl hydroxysulfobetaine, and the like.

The amphoteric surfactant of component (F) can be used alone or in combination of two or more kinds. The content of the component (F) in the first composition is preferably 0.01% by mass or more, more preferably 0.5% by mass or more, more preferably 1.0% by mass or more, and preferably 15% by mass or less, more preferably 10% by mass or less, and still more preferably 5% by mass or less from the viewpoint of obtaining high detergency and good foaming effect.

<Component (C): Aromatic Sulfonic Acid or Salt Thereof>

It is preferable that the first composition does not contain the active component (C) included in the second composition described later, that is, the content of the component (C) is 0% by mass, from the viewpoints of improving the setting of the hair bundle after drying, stress relaxation rate of the dried hair, formability when stress is applied to the dried hair, and smoothness of the hair bundle after drying. Further, even when the component (C) is included, the content of the component (C) in the first composition is preferably less than 3% by mass, more preferably less than 1% by mass.

The first composition uses water as a medium, but lower alcohols such as ethanol can also be used in combination as a medium other than water.

The first composition can be used as a hair cleanser composition, a hair conditioning composition, or a hair treatment composition, among which it is preferable to use it as a hair cleansing composition. The dosage form of the first composition may take any form, such as a liquid, an emulsion, a gel, a cream, or a foam.

<pH>

The pH of the first composition is preferably 2.0 or more, more preferably 2.5 or more, more preferably 3.0 or more, and preferably 7.0 or less, more preferably 5.5 or less, and still more preferably 4.5 or less from the viewpoints of improving the setting of hair bundles after drying, the stress relaxation rate of the dried hair, and the formability when stress is applied to the dried hair. The pH is a value at 25° C. when diluted 20 times with water, and the pH was measured by a glass-electrode measuring method using a HM-30R mold manufactured by DKK-TOA Corporation.

[Secondary Composition]

The second composition is a hair treatment agent containing as component (C) an aromatic sulfonic acid having a molecular weight of 300 or less or a salt thereof, wherein the weight ratio (H)/(C) of the component (H) cationic surfactant to the component (C) is less than 1.

<Component (C): An Aromatic Sulfonic Acid Having a Molecular Weight of 300 or Less or a Salt Thereof>

Examples of the aromatic sulfonic acid having a molecular weight of 300 or less of the component (C) or a salt thereof include naphthalene sulfonic acids, azulene sulfonic acids, benzophenone sulfonic acids, benzene sulfonic acids, and the like.

Examples of the naphthalene sulfonic acids include compounds represented by the following general formula (4).

[Formula 2]

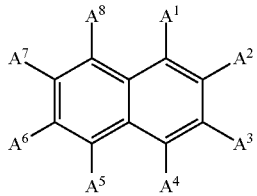

(4)

[wherein one or more of the $A^1$-$A^8$ represents a sulfo group or salts thereof, and the remainder represents a hydrogen atom, halogen atom, hydroxy group, nitro group, carboxy group, a lower alkoxycarbonyl group, an alkyl group, an alkenyl group, a lower alkoxy group, a formyl group, an acyl group, a phenylazo group which may have substituent group or —N(R') (R") (R' and R' represents a hydrogen atom, a lower alkyl group, a lower alkenyl group, a phenyl group, a benzyl group, or an acyl group).

Examples of the naphthalene sulfonic acids include 1- or 2-naphthalene sulfonic acid (α- or β-naphthalene sulfonic acid), 2,7-naphthalene disulfonic acid, 1,5-naphthalene disulfonic acid, 2,6-naphthalene disulfonic acid, 2,7-naphthalene disulfonic acid, 1-naphthol-2-sulfonic acid, 1-naphthol-4-sulfonic acid, 2-naphthol-6-sulfonic acid, 2,3-dihydroxynaphthalene-6-sulfonic acid, and 1,7-dihydroxynaphthalene-3-sulfonic acid, S acid (1-amino-8-naphthol-4-sulfonic acid), gamma acid (2-amino-8-naphthol-6-sulfonic acid), J acid (2-amino-5-naphthol-7-sulfonic acid), 1-amino-2-naphthol-4-sulfonic acid, 1-naphthylamine-4-sulfonic acid, Bronner's acid (2-naphthylamine-6-sulfonic acid), and Cleve's acid(1-naphthylamine-7-sulfonic acid), 2-naphthylamine-1-sulfonic acid, 1-naphthylamine-6-sulfonic acid, 1-naphthylamine-8-sulfonic acid, 2,7-diamino-1-naphthol-3-sulfonic acid, 7,8-diamino-1-naphthol-3-sulfonic acid, formalin polycondensate of naphthalenesulfonic acid having a molecular weight of 300 or less, 6-methyl-2-naphthalene sulfonic acid, 4-ethyl-1-naphthalenesulfonic acid, 5-isopropyl-1-naphthalenesulfonic acid, 5-butyl-2-naphthalenesulfonic acid, and salts thereof.

Examples of azulene sulfonic acids include guaiazulene sulfonic acid, 1-azulene sulfonic acid, 3-acetyl-7-isopropyl-1-azulene sulfonic acid, 3-(2-hydroxyethyl)-7-isopropyl-1-azulene sulfonic acid, 3-methyl-7-isopropyl-1-azulensulfonic acid, 7-isopropyl-1-azulene sulfonic acid, 1,4-dimethyl-7-isopropyl-2-azulene sulfonic acid, 4-ethoxy-3-ethyl-6-isopropyl-1-azulene sulfonic acid, 1,3-azulene disulfonic acid(1,1-dimethylethyl)-5-azulene sulfonic acid, 3-formyl-4,6,8-trimethyl-1-azulene sulfonic acid and salts thereof.

Examples of the benzophenone sulfonic acids include compounds represented by the following general formula (5).

[3]

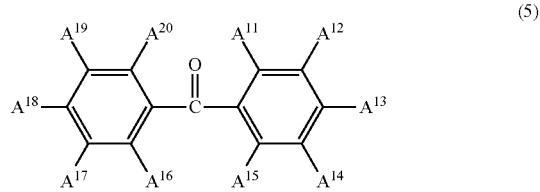

(5)

[wherein one or more of the $A^{11}$-$A^{20}$ represents a sulfo group or salt thereof, and the remainder represents a hydrogen atom, a halogen atom, a hydroxy group, a carboxy group, an amino group, a lower alkyl group, a lower alkenyl group, a lower alkoxy group or an acyl group]

Specific examples of the benzophenone sulfonic acids include oxybenzenesulfonic acid, o-chlorobenzophenone sulfonic acid, p-chlorobenzophenone sulfonic acid, 2-hydroxybenzophenone sulfonic acid, 4-hydroxybenzophenone sulfonic acid, 2-aminobenzophenone sulfonic acid, 4-aminobenzophenone sulfonic acid, 2-methylbenzophenone sulfonic acid, 4-methoxybenzophenone sulfonic acid, 4,4'-dimethylbenzophenone sulfonic acid, 4,4'-dimethoxybenzophenone sulfonic acid, and salts thereof.

Examples of the benzenesulfonic acids include compounds represented by the following general formula (6).

[4]

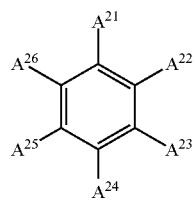

(6)

[wherein one or more of the $A^{21}$-$A^{26}$ represents a sulfo group or a salt thereof, and the remainder represents a hydrogen atom or a lower alkyl group]

Examples of benzenesulfonic acid include benzenesulfonic acid, o-toluensulfonic acid, p-toluensulfonic acid, xylenesulfonic acid, cumene sulphonic acid, ethylbenzenesulfonic acid, 2,4,6-trimethylbenzenesulfonic acid, and their salt.

Salts of the above aromatic sulfonic acids include sodium, potassium, lithium, aluminum, ammonium, and organic quaternary ammonium salts.

As the aromatic sulfonic acid or its salt of the component (C), naphthalene sulfonic acids represented by the general formula (4), benzophenone sulfonic acids represented by the general formula (5), and benzene sulfonic acids represented by the general formula (6) are preferable from the viewpoints of improving the setting of hair bundles after drying, the stress relaxation rate of dry hair, and the formability when stress is applied to dry hair, and further, 2-naphthalene sulfonic acid (β-naphthalene sulfonic acid), 1-naphthalene sulfonic acid (α-naphthalene sulfonic acid), p-toluene sulfonic acid, xylene sulfonic acid, hydroxymethoxybenzophenone sulfonic acid (Oxybenzone-5), and salts thereof are more preferable. Among these, p-toluenesulfonic acid, 1- or 2-naphthalenesulfonic acid (α- or β-naphthalenesulfonic acid) or a salt thereof is more preferable from the above viewpoint.

These aromatic sulfonic acids or salts thereof can be used alone or in combination of two or more kinds. The content of the component (C) in the second composition is preferably 0.1% by mass or more, more preferably 0.5% by mass or more, more preferably 1.0% by mass or more, more preferably 1.5% by mass or more, still more preferably 2.0% by mass or more, still more preferably 2.5% by mass or more, and preferably 15% by mass or less, more preferably 12% by mass or less, still more preferably 10% by mass or less, still more preferably 8% by mass or less, still more preferably 6% by mass or less, and still more preferably 4% by mass or less, from the viewpoints of improving the setting of the hair bundles after drying, the stress relaxation rate of the dried hair when applying stress to the dried hair, and the smoothness of the hair bundle after drying.

<Component (H): Cationic Surfactant>

The second composition may contain, but preferably does not contain, a cationic surfactant as component (H), and even if it contains component (H), the mass ratio (H)/(C) of component (H) to component (C) in the second composition is less than 1, preferably less than 0.8, more preferably less than 0.6, still more preferably less than 0.4, still more preferably less than 0.2, and still more preferably 0. This is because component (H) forms an association with the aromatic sulfonic acid of component (C) to prevent the penetration of component (C) into the hair interior from being inhibited, so that the hair bundle after drying is consolidated, the stress relaxation rate of the dry hair, and the formability when stress is applied to the dry hair are improved. Cationic surfactants for such component (H) include quaternary ammonium salts and tertiary amines and salts thereof. More specifically, a cationic surfactant described in Japanese Patent Application Laid-Open No. 2017-19748 can be cited.

In addition, the content of the component (H) in the second composition is preferably less than 6.0% by mass, more preferably less than 5.0% by mass, more preferably less than 4.0% by mass, still more preferably less than 3.0% by mass, still more preferably less than 2.0% by mass, still more preferably less than 1.0% by mass, still more preferably less than 0.5% by mass, and still more preferably 0% by mass, from the above viewpoint.

<Component (A): A Carboxylic Acid Whose Inorganic and Organic Values are within a Specified Range, or a Salt of the Carboxylic Acid>

It is preferable that the second composition further contains, as the component (A), a carboxylic acid having an inorganic value of 230 or more and 450 or less inclusive and an organic value of from 50 or more and 250 or less, or a salt of the carboxylic acid, from the viewpoints of improving the setting of hair bundles after drying, stress relaxation rate of dry hair, formability when stress is applied to dry hair, and smoothness of hair bundles after drying. Such carboxylic acids or salts thereof can be the same as those of the above-mentioned first composition, and among them, succinic acid, malic acid, lactic acid, mandelic acid and salts thereof are preferable from the above-mentioned viewpoints, and succinic acid, malic acid and salts thereof are more preferable from the viewpoints of the improving the setting of hair bundles after drying, the stress relaxation rate of dry hair formability when stress is applied to dry hair, and succinic acid and salts thereof are more preferable.

These carboxylic acids or salts thereof can be used alone or in combination of two or more kinds. The content of the component (A) in the second composition is preferably 0.1% by mass or more, more preferably 0.3% by mass or more, more preferably 0.5% by mass or more, still more preferably 1.0% by mass or more, and more preferably 5% by mass or less, more preferably 4.0% by mass or less, still more preferably 3.5% by mass or less, and still more preferably 3% by mass or less from the viewpoints of improving the setting of the hair bundles after drying, stress relaxation rate of the dried hair, and formability when stress is applied to the dried hair.

<Component (E): Nonionic Surfactant>

The second composition may further contain a nonionic surfactant as component (E). As the nonionic surfactant, the same as the first composition described above can be used, and among them, polyoxyalkylene alkyl ether and polyoxyalkylene alkenyl ether are preferable.

The nonionic surfactant of component (E) can be used alone or in combination of two or more. The content of the component (E) in the second composition is preferably 0.01% by mass or more, more preferably 0.05% by mass or more, more preferably 0.10% by mass or more, more preferably 10% by mass or less, more preferably 5% by mass or less, and still more preferably 2% by mass or less from the viewpoint of facilitating uniform application of the composition to hair.

<Component (G): Aromatic Alcohol>

It is preferable that the second composition further contains an aromatic alcohol as the component (G) from the viewpoint of improving the setting of the hair bundle after drying. Examples of such aromatic alcohols include benzyl alcohol, cinnamyl alcohol, phenethylalcohol, p-anisyl alcohol, p-methylbenzyl alcohol, phenoxyethanol, 2-benzyloxyethanol, and the like. Among these, benzyl alcohol is preferable from the viewpoint of sufficiently penetrating the component (C) in the second composition into the hair and improving the setting of the hair bundle after drying.

Any of these aromatic alcohols can be used alone or in combination of two or more kinds. The content of the component (G) in the second composition is preferably 0.1% by mass or more, more preferably 0.5% by mass or more, more preferably 0.8% by mass or more, still more preferably 1.0% by mass or more, and more preferably 10% by mass or less, more preferably 5.0% by mass or less, still more preferably 4.0% by mass or less, and still more preferably 3.0% by mass or less from the viewpoint of improving the setting of the hair bundles after drying, the stress relaxation rate of the dried hair, and the formability when stress is applied to the dried hair.

In the second composition, the mass ratio (C)/(G) of the component (C) to the component (G) is preferably 0.5 or more, and preferably 0.6 or more, still more preferably 0.8 or more, still more preferably 1.0 or more, still more preferably 1.1 or more, still more preferably 1.2 or more, still more preferably 5.5 or less, still more preferably 4.5 or less, still more preferably 4.0 or less, still more preferably 3.5 or less, still more preferably 3.2 or less, and still more preferably 3.0 or less from the viewpoint of improving the setting and smoothness of the hair bundles after drying.

<Component (B): Anionic Surfactant>

It is preferable that the second composition does not include the anionic surfactant of the component (B) included in the first composition, that is, the content of the component (B) is 0% by mass, from the viewpoint of improving the setting and smoothness of the hair bundle after drying. Even when the component (B) is included, the content of the component (B) in the second composition is preferably less than 1% by mass, more preferably less than 0.5% by mass.

The second composition uses water as a medium, but lower alcohols such as ethanol can also be used in combination as a medium other than water.

The second composition is preferably used as a hair conditioning composition, a hair treatment composition. The dosage form of the second composition may take any form, such as a liquid, an emulsion, a gel, a cream, or a foam.

<pH>

The pH of the second composition is preferably 3.0 or more, more preferably 4.0 or more, more preferably 5.0 or more, and preferably 10.0 or less, more preferably 7.0 or less, and still more preferably 6.5 or less from the viewpoints of improving the setting of hair bundles after drying, the stress relaxation rate of the dried hair, and the formability when stress is applied to the dried hair. The pH is a value at 25° C. when diluted 20 times with water, and the pH was measured by a glass-electrode measuring method using a HM-30R mold manufactured by DKK-TOA Corporation.

<Third Composition>

The multi-agent type hair treatment agent of the present invention preferably comprises a third composition containing a cationic surfactant as the component (H) and a higher alcohol as the component (I), in addition to the first and second compositions described above, from the viewpoints of improving the setting of hair bundles after drying, stress relaxation rate of dry hair, and smoothness of hair bundles after drying.

<Component (H): Cationic Surfactant>

Cationic surfactants of component (H) include quaternary ammonium salts and tertiary amines and salts thereof, as well as component (H) in the second composition described above. More specifically, a cationic surfactant described in Japanese Patent Application Laid-Open No. 2017-19748 can be used.

The cationic surfactant of component (H) can be used alone or in combination of two or more kinds. The content of the component (H) in the third composition is preferably 0.1% by mass or more, more preferably 0.5% by mass or more, still more preferably 1% by mass or more, still more preferably 2.0% by mass or more, and preferably 10% by mass or less, still more preferably 6% by mass or less, still more preferably 4% by mass or less, and still more preferably 3.5% by mass or less from the viewpoint of softening the hair when rinsing off and smoothing the hair after drying.

<Component (I): Higher Alcohol>

As for the higher alcohol of component (I), the following general formula (12) can be used.

$$R^{20}-OH \quad (12)$$

[In the formula, $R^{20}$ represents a straight or branched chain hydrocarbon group having 12 carbon atoms or more and 24 carbon atoms or less]

Examples of the component (I) include lauryl alcohol, myristyl alcohol, cetyl alcohol, stearyl alcohol, cetearyl alcohol, aralkyl alcohol, behenyl alcohol, oleyl alcohol, and the like, among which cetyl alcohol, stearyl alcohol, cetearyl alcohol, and behenyl alcohol are preferable.

Component (I) can be used alone or in combination of two or more. The content of the component (I) in the third composition is preferably 0.5% by mass or more, more preferably 3% by mass or more, still more preferably 5% by mass or more, and preferably 15% by mass or less, more preferably 12% by mass or less, and still more preferably 9% by mass or less from the viewpoints of improving the setting of the hair bundles after drying and suppressing the stickiness of the hair after drying.

<Component (G): Aromatic Alcohol>

The third composition may further contain an aromatic alcohol as component (G) from the viewpoint of improving the setting of the hair bundle after drying. As the aromatic alcohol, it is possible to use the same aromatic alcohol as that mentioned in the second composition, and among them, benzyl alcohol is preferable from the viewpoint of improving the setting of the hair bundle after drying and imparting tension/stiffness to the hair after drying.

Any of these aromatic alcohols can be used alone or in combination of two or more kinds. The content of the component (G) in the third composition is preferably 0.01% by mass or more, more preferably 0.05% by mass or more, more preferably 0.10% by mass or more, and preferably 10% by mass or less, more preferably 5% by mass or less, and still more preferably 3% by mass or less from the viewpoints of improving the setting of the hair bundle after drying and imparting tension/stiffness the hair after drying.

<Component (A): A Carboxylic Acid Whose Inorganic and Organic Values are within a Specified Range, or a Salt of the Carboxylic Acid>

The third composition preferably further contains, as component (A), a carboxylic acid having an inorganic value of 230 or more and 450 or less and an organic value of 50 or more and 250 or less, or a salt of the carboxylic acid, from the viewpoints of improving the setting of hair bundles after drying, stress relaxation rate of dry hair, formability when stress is applied to dry hair, and smoothness of hair bundles after drying. Such carboxylic acids or salts thereof may be similar to the first and second compositions described above.

These carboxylic acids or salts thereof can be used alone or in combination of two or more kinds. The content of component (A) in the third composition is, from the viewpoint of improving the stress relaxation rate of dry hair, formability when stress is applied to dry hair, is preferred 0.1% by mass or more, more preferably 0.3% by mass or more, more preferably 0.5% by mass or more, more preferably 1.0% by mass or more, and preferably 5% by mass or less, more preferably 4.0% by mass or less, more preferably 3.5% by mass or less, more preferably 3.0% by mass or less, and more preferably 2.5% by mass or less.

The third composition uses water as a medium, but lower alcohols such as ethanol can also be used in combination as a medium other than water.

The third composition is preferably used as a hair conditioning composition, a hair treatment composition. The dosage form of the third composition may take any form, such as a liquid, an emulsion, a gel, a cream, or a foam.

<pH>

The pH of the third composition is preferably 2.0 or more, more preferably 2.5 or more, more preferably 3.0 or more, and preferably 10.0 or less, more preferably 8.0 or less, and still more preferably 6.0 or less, from the viewpoint of improving the setting of the hair bundles after drying. The pH was a value at 25° C. when diluted 20 times with water, and the pH was measured by a glass-electrode measuring method using a HM-30R mold manufactured by DKK-TOA Corporation.

[Hair Treatment Method]

The hair treatment method of the present invention comprises the following steps (i) to (ii).

Step (i): applying and rinsing off the first composition containing component (A) and component (B) to hair Step (ii): after step (i), applying to the hair a second composition containing component (C) and having a weight ratio (H)/(C) of component (H) to component (C) of less than 1

<Step (i): Applying the First Composition to the Hair and Rinsing Off>

In step (i), the first composition may be applied to either dry hair or wet hair, but it is preferably applied to wet hair from the viewpoint of better packing of the tufts after finger passage and drying during processing.

The amount of the first composition to be applied to the hair in step (i) is preferably 0.05 or more, more preferably 0.07 or more, still more preferably 0.09 or more, and preferably 0.20 or less, more preferably 0.17 or less, still more preferably 0.15 or less in terms of the ratio of the bath to the dry weight of the hair (the weight of the first composition/the dry weight of the hair).

After the first composition is applied to the hair, the composition may be evenly distributed through the hair by hand, for example, by kneading the hair with the composition or finger-combing.

<Step (ii) Applying the Second Composition to the Hair>

After step (i) and before step (ii), the hair may or may not be towel dried.

The amount of the second composition to be applied to the hair in step (ii) is preferably 0.05 or more, more preferably 0.07 or more, still more preferably 0.09 or more, and preferably 0.20 or less, more preferably 0.17 or less, still more preferably 0.15 or less in terms of the bath ratio to the dry weight of the hair (mass of the second composition/dry weight of the hair).

After the second composition is applied to the hair, the composition may be evenly distributed through the hair by hand, for example, by kneading the hair with the composition or finger-combing.

In the case where the step of applying still another composition to the hair, such as the step (iii) described later, is not performed after the step (ii), the second composition on the hair may be rinsed or not rinsed, but it is preferable to rinse the second composition from the viewpoint of making the hair feel lighter and less tangled after the treatment. In this case, it is preferable to include a step of allowing the component (C) in the second composition to sufficiently permeate into the hair interior, and leaving the hair to which the second composition has been applied after the step (ii) for 1 to 30 minutes, and for 1 to 10 minutes from the viewpoint of convenient treatment, at 15 to 60° C. before rinsing of f the second composition on the hair, from the viewpoints of improving the setting of the dried hair bundle, stress relaxation rate of the dried hair, formability when stress is applied to the dried hair, and smoothness of the dried hair bundle.

<Step (iii): Applying a Third Composition to Hair>

Step (iii) is the step of applying to the hair, after step (ii), optionally a third composition comprising a cationic surfactant and a higher alcohol, with a view to improving the smoothness of the hair bundle after drying.

When performing step (iii), the second composition on the hair may or may not be rinsed off prior to step (iii), but it is preferable not to rinse off from the viewpoint of sufficiently penetrating the component (C) in the second composition into the hair interior, whereby improving the setting of the dried hair bundle, stress relaxation rate of the dried hair, formability when stress is applied to the dried hair, and smoothness of the dried hair bundle.

In the case of rinsing off the second composition on the hair before step (iii), it is preferable to include a step of leaving the hair to which the second composition has been applied for 1 to 30 minutes, and for 1 to 10 minutes from the viewpoint of convenient treatment, at 15 to 60° C. before rinsing off the second composition on the hair after step (ii) from the viewpoints of improving the setting of the hair bundles after drying, stress relaxation rate of the dried hair, and formability when stress is applied to the dried hair.

The amount of the third composition to be applied to the hair in step (iii) is preferably 0.05 or more, more preferably 0.07 or more, still more preferably 0.09 or more, and preferably 0.2 or less, more preferably 0.17 or less, still more preferably 0.15 or less in terms of the bath ratio of the dry weight of the hair to the dry weight of the hair (mass of the third composition/dry weight of the hair).

After the third composition is applied to the hair, the composition may be evenly distributed through the hair by hand, for example, by kneading the hair with the composition or finger-combing.

After step (iii), the third composition on the hair, or the second composition and the third composition on the hair, may or may not be rinsed, but it is preferable to rinse from the viewpoint of improving the lightness of the hand of the hair after the treatment and suppressing the stickiness of the hair after the drying.

In the case of rinsing, it is preferable to include a step of leaving the hair to which the third composition has been applied for 1 to 30 minutes, and for 3 to 10 minutes from the viewpoint of convenient treatment, at 15 to 60° C. between the step (iii) and the rinsing step, from the viewpoints of improving the setting of the hair bundles after drying, stress relaxation rate of the dried hair, and formability when stress is applied to the dried hair.

After the step of rinsing off the composition on the hair in step (ii) or (iii), the hair may or may not be dried, but from the viewpoint of preventing damage to the hair, drying is preferred. The hair can be dried by towel drying, natural drying, heating drying such as a dryer, or the like.

From the viewpoints of the improving of the setting of the hair bundles after drying, the stress relaxation rate of the dried hair, and the formability when stress is applied to the dried hair, it is preferable to arrange the hair using hand or a tool such as a comb or a brush during the drying process and after the drying process. If it is desired to shape the hair, it is preferable to use hair irons, electric rods, curlers, hot curlers, etc. during and after the drying process. Even if an undesirable shape is formed after drying, it can be set cleanly so that shaping can be performed again.

As described above, in the present invention, not only the consistency when the wet hair is dried but also the formability for the hair after drying are excellent, and moreover, smoothness can be imparted to the hair.

Preferred embodiments of the present invention are further disclosed below with respect to the embodiments described above.

<1>

A multi-agent type hair treatment agent comprising
a first composition containing component (A) and component (B); and
a second composition containing component (C),
wherein the weight ratio (H)/(C) of component (H) to component (C) in the second composition is less than 1.

Component (A): a carboxylic acid having an inorganic value of 230 or more and 450 or less and an organic value of 50 or more and 250 or less, or a salt of the carboxylic acid Component (B): anionic surfactant Component (C): an aromatic sulfonic acid having a molecular weight of 300 or less or a salt thereof Component (H): cationic surfactant

<2>

The multi-agent type hair treatment agent according to <1>, wherein the inorganic value of the component (A) is 265 or more and 400 or less, and the organic value of the component (A) is 60 or more and 180 or less.

<3>
The multi-agent type hair treatment agent according to <1> or <2>, wherein the component (A) is selected from succinic acid, malic acid, lactic acid, mandelic acid and salts thereof.

<4>
The multi-agent type hair treatment according to <1> or <2> where component (A) is selected from among succinic acid, malic acid and these salt.

<5>
The multi-agent type hair treatment agent according to any one <1> to <4>, wherein the content of the component (A) in the first composition is 0.1% by mass or more and 5% by mass or less.

<6>
The multi-agent type hair treatment agent according to any one of <1> to <4>, wherein the content of the component (A) in the first composition is 0.3% by mass or more and 3.0% by mass or less.

<7>
The multi-agent type hair treatment agent according to any one of <1> to <6>, wherein the component (B) is represented by the following general formula (2) or (3).

$$R^2O(CH_2CH_2O)_mSO_3M \quad (2)$$

$$R^2OSO_3M \quad (3)$$

[wherein, $R^2$ represents an alkyl group or an alkenyl group having 10 to 18 carbons, and preferred an alkyl group having 12 to 14 carbons, M represents an alkali metal, an alkaline-earth metal or ammonium, and m represents a number of 1 to 30 of weight averages].

<8>
The multi-agent type hair treatment agent according to any one of <1> to <7>, wherein the content of the component (B) in the first composition is 1% by mass or more and 30% by mass or less.

<9>
The multi-agent type hair treatment agent according to any one of <1> to <8>, wherein the first composition further contains a cationic polymer as component (D).

<10>
The multi-agent type hair treatment agent according to <9>, wherein component (D) is selected from cationized cellulose and cationized guar gum.

<11>
The multi-agent type hair treatment agent according to <9> or <10>, wherein the content of the component (D) in the first composition is 0.01% by mass or more and 5% by mass or less.

<12>
The multi-agent type hair treatment agent according to <9> or <10>, wherein the content of the component (D) in the first composition is 0.10% by mass or more and 1% by mass or less.

<13>
The multi-agent type hair treatment agent according to any one of <1> to <12>, wherein the first composition further contains a nonionic surfactant as component (E).

<14>
The multi-agent type hair treatment agent according to <13> wherein component(E) is selected from polyoxyalkylene alkyl ether, polyoxyalkylene alkenyl ether, alkylglyceryl ether and alkenylglyceryl ether.

<15>
The multi-agent type hair treatment according to <13> or <14> where the content of the component (E) in the first composition is 0.01% by mass or more and 15% by mass or less.

<16>
The multi-agent type hair treatment agent according to any one of <1> to <15>, wherein the first composition further contains a amphoteric surfactant as component (F).

<17>
The multi-agent type hair treatment agent according to <16>, wherein the content of the component (F) in the first composition is 0.01% by mass or more and 15% by mass or less.

<18>
The multi-agent type hair treatment agent according to any one of the <1> to <17>, wherein the content of the component (C) in the first composition is less than 3% by mass.

<19>
The multi-agent type hair treatment agent according to any one of the <1> to <17>, wherein the content of the component (C) in the first composition is less than 1% by mass.

<20>
The multi-agent type hair treatment agent according to any one of <1> to <19>, wherein the pH at 25° C. when the first composition is diluted 20 times with water is 2.0 or more and 7.0 or less.

<21>
The multi-agent type hair treatment agent according to any one of <1> to <19>, wherein the pH at 25° C. when the first composition is diluted 20 times with water is 3.0 or more and 4.5 or less.

<22>
The multi-agent type hair treatment agent according to any one of <1> to <21>, wherein the component (C) contained in the second composition is selected from naphthalene sulfonic acids, azulene sulfonic acids, benzophenone sulfonic acids, and benzene sulfonic acids.

<23>
The multi-agent type hair treatment agent according to any one of <1> to <21>, wherein the component (C) contained in the second composition is selected from p-toluenesulfonic acid, 1-naphthalenesulfonic acid, 2-naphthalenesulfonic acid and salts thereof.

<24>
The multi-agent type hair treatment agent according to any one of the <1> to <23>, wherein the content of the component (C) in the second composition is 0.1% by mass or more and 15% by mass or less.

<25>
The multi-agent type hair treatment agent according to any one of the <1> to <23>, wherein the content of the component (C) in the second composition is 1.5% by mass or more and 6% by mass or less.

<26>
The multi-agent type hair treatment agent according to any one of <1> to <25>, wherein the second composition further contains component (A).

<27>
The multi-agent type hair treatment agent according to <26>, wherein the content of the component (A) in the second composition is 0.1% by mass or more and 5% by mass or less.

<28>

The multi-agent type hair treatment agent according to <26>, wherein the content of the component (A) in the second composition is 0.3% by mass or more and 4.0% by mass or less.

<29>

The multi-agent type hair treatment agent according to any one of <1> to <28>, wherein the second composition further contains component (E).

<30>

The multi-agent type hair treatment agent according to <29>, wherein the content of the component (E) in the second composition is 0.01% by mass or more and 10% by mass or less.

<31>

The multi-agent type hair treatment agent according to any one of <1> to <30>, wherein the second composition further contains an aromatic alcohol as component (G).

<32>

The multi-agent type hair treatment agent according to <31>, wherein the component (G) is selected from benzyl alcohol and phenoxyethanol.

<33>

The multi-agent type hair treatment according to <31> or <32> where the content of the component (G) in the second composition is 0.1% by mass or more and 10% by mass or less.

<34>

The multi-agent type hair treatment agent according to <31> or <32>, wherein the content of the component (G) in the second composition is 0.5% by mass or more and 4.0% by mass or less.

<35>

The multi-agent type hair treatment agent according to any one of <31> to <34>, wherein the weight ratio (C)/(G) of the component (C) to the component (G) in the second composition is 0.5 or more and 5.5 or less.

<36>

The multi-agent type hair treatment agent according to any one of <1> to <35>, wherein the content of the component (B) in the second composition is less than 1% by mass.

<37>

The multi-agent type hair treatment agent according to any one of <1> to <35>, wherein the content of the component (B) in the second composition is 0% by mass.

<38>

The multi-agent type hair treatment agent according to any one of <1> to <37>, wherein the mass ratio (H)/(C) of the component (H) to the component (C) in the second composition is less than 0.8.

<39>

The multi-agent type hair treatment agent according to any one of <1> to <38>, wherein the mass ratio (H)/(C) of the component (H) to the component (C) in the second composition is less than 0.4.

<40>

The multi-agent type hair treatment agent according to any one of <1> to <38>, wherein the mass ratio (H)/(C) of the component (H) to the component (C) in the second composition is 0.

<41>

The multi-agent type hair treatment agent according to any one of the <1> to <40>, wherein the content of the (H) cationic surfactant in the second composition is less than 0.5% by mass.

<42>

The multi-agent type hair treatment agent according to any one of <1> to <40>, wherein the content of the (H)cationic surfactant in the second composition is 0% by mass.

<43>

The multi-agent type hair treatment agent according to any one of <1> to <42>, wherein the pH of the second composition is 3.0 or more and 7.0 or less.

<44>

The multi-agent type hair treatment agent according to any one of <1> to <43>, further comprising a third composition containing a cationic surfactant as component (H) and a higher alcohol as component (I).

<45>

The multi-agent type hair treatment agent according to <44>, wherein the content of the component (I) in the third composition is 0.5% by mass or more and 15% by mass or less.

<46>

The multi-agent type hair treatment agent according to <44> or <45>, wherein the pH of the third composition is 2.0 or more and 10.0 or less.

<47>

A hair treatment method comprising the following steps (i) to (ii):

Step (i): applying and rinsing off the first composition containing component (A) and component (B) to hair Step (ii): after step (i), applying to the hair a second composition containing component (C) and having a weight ratio (H)/(C) of component (H) to component (C) of less than 1

Component (A): a carboxylic acid having an inorganic value of 230 or more and 450 or less and an organic value of 50 or more and 250 or less, or a salt of the carboxylic acid Component (B): anionic surfactant Component (C): an aromatic sulfonic acid having a molecular weight of 300 or less or a salt thereof Component (H): cationic surfactant

<48>

The hair treatment method according to <47>, wherein the amount of the first composition applied to the hair in step (i) is 0.05 or more and 0.15 or less in terms of a bath ratio (mass of the first composition/dry mass of the hair) to the dry mass of the hair.

<49>

The hair treatment method according to <47> or <48>, wherein the amount of the second composition to be applied to the hair in step (ii) is 0.05 or more and 0.20 or less in terms of the bath ratio to the dry weight of the hair (the weight of the first composition/the dry weight of the hair).

<50>

The hair treatment method according to any one of <47> to <49>, further comprising the step of rinsing off the second composition on the hair after step (ii) and then not comprising the step of applying a further composition to the hair.

<51>

The hair treatment method of <50> comprising the step of leaving the hair to which the second composition has been applied for 1 to 30 minutes at 15 to 60° C. after step (ii) and before rinsing off the second composition on the hair.

<52>

The hair treatment method according to any one of <47> to <49>, further comprising step (iii) after step (ii).

Step (iii): applying to the hair a third composition comprising a cationic surfactant and a higher alcohol

<53>

The hair treatment method according to <52>, wherein the amount of the third composition to be applied to the hair in step (iii) is 0.05 or more and 0.20 or less in terms of a bath ratio (mass of the third composition/dry mass of the hair) to the dry mass of the hair.

<54>

The hair treatment method of <52> or <53> comprising the step of rinsing the second composition on the hair after step (ii) and prior to step (iii).

<55>

The hair treatment method of <54> comprising the step of leaving the hair to which the second composition has been applied for 1 to 30 minutes at 15 to 60° C. after step (ii) and before rinsing off the second composition on the hair.

<56>

The hair treatment method according to <52> or <53>, wherein the second composition on the hair is not rinsed after step (ii) and prior to step (iii).

<57>

The hair treatment method according to any one of <52> to <56>, comprising the step of rinsing the third composition on the hair after step (iii).

EXAMPLES

Examples 1 to 16, Comparative Examples 1 to 6

A first composition (hair cleansing composition A) of the composition shown in Table 1, a second composition (hair cosmetic composition B) of the composition shown in Table 2, and a third composition (hair cosmetic composition C) of the composition shown in Table 3 were prepared and evaluated using Japanese curly hair having no history of chemical treatment. Evaluation results are given in Table 4 to 6.

(pH Measurement Method)

The pH of the sample was measured at 25° C. using a pH meter (manufactured by DKK-TOA CORPORATION, type HM-30R) after the sample was diluted 20 times by weight with purified water and dissolved by stirring,

TABLE 1

| | First composition | Hair cleansing composition A(% by mass) | | | | | | | | | | |
|---|---|---|---|---|---|---|---|---|---|---|---|---|
| | | A1 | A2 | A3 | A4 | A5 | A6 | A7 | A8 | A9 | A10 | A11 |
| (A) | Succinic acid | 1.2 | 1.2 | — | — | — | 5.0 | 0.1 | 0.3 | 0.8 | 2.0 | 3.0 |
| | Malic acid | — | — | 1.2 | — | — | — | — | — | — | — | — |
| | Lactic acid | — | — | — | 1.2 | — | — | — | — | — | — | — |
| | Mandelic acid | — | — | — | — | 1.2 | — | — | — | — | — | — |
| | Phenyl lactic acid | — | — | — | — | — | — | — | — | — | — | 1.0 |
| (B) | Sodium laureth ammonium | 11.5 | 11.5 | 11.5 | 11.5 | 11.5 | 30.0 | 1.0 | 2.9 | 5.0 | 14.0 | 19.0 |
| | Sodium laureth sulfate | — | — | — | — | — | — | — | 0.1 | — | — | — |
| | Sodium Laureth-4 carboxylate | — | — | — | — | — | — | — | — | — | 1.0 | — |
| | Sodium taurine cocoly methyltarate (*1) | — | — | — | — | — | — | — | — | — | — | 1.0 |
| (C) | p-Toluene sulfonic acid | — | 2.0 | — | — | — | — | — | — | — | — | — |
| | β-Naphthalenesulfonic acid Na | — | 1.0 | — | — | — | — | — | — | — | — | — |
| | Xylene sulfonic acid Na | — | — | — | — | — | — | — | — | — | — | 1.0 |
| (D) | Polyquaternium-10(*2) | 0.35 | 0.35 | 0.35 | 0.35 | 0.35 | 0.35 | 0.35 | 0.01 | 0.1 | 0.9 | 4.8 |
| | Guar hydroxy propyltrimonium chloride | — | — | — | — | — | — | — | — | — | 0.1 | — |
| | Polyquaternium-52 (*3) | — | — | — | — | — | — | — | — | — | — | 0.1 |
| | Polyquaternium-67 (*4) | — | — | — | — | — | — | — | — | — | — | 0.1 |
| (E) | Isodecyl glyceryl ether | 0.5 | 0.5 | 0.5 | 0.5 | 0.5 | 0.5 | 0.5 | 12.4 | 2.4 | 0.1 | 0.01 |
| | PPG-3 Caprylyl Ether (*5) | 0.75 | 0.75 | 0.75 | 0.75 | 0.75 | 0.75 | 0.75 | 0.5 | 0.5 | — | — |
| | Laureth-3 (*6) | 0.2 | 0.2 | 0.2 | 0.2 | 0.2 | 0.2 | 0.2 | 0.2 | 0.2 | — | — |
| | Laureth-16 | 1.8 | 1.8 | 1.8 | 1.8 | 1.8 | 1.8 | 1.8 | 1.8 | 1.8 | — | 0.15 |
| | Cocamide MEA | — | — | — | — | — | — | — | 0.1 | — | — | — |
| | PPG-7 (*7) | — | — | — | — | — | — | — | — | 0.1 | — | — |
| (F) | Laury Hydroxysultaine (*8) | 0.8 | 0.8 | 0.8 | 0.8 | 0.8 | 0.8 | 0.8 | 0.01 | 0.3 | 1.2 | 3.8 |
| | Lauramidopropyl betaine (*9) | 2.4 | 2.4 | 2.4 | 2.4 | 2.4 | 2.4 | 2.4 | — | 0.7 | 3.8 | 11.2 |
| (G) | Benzyl alcohol | — | — | — | — | — | — | — | 9.0 | 3.0 | 1.0 | 0.1 |
| | Phenoxyethanol | — | — | — | — | — | — | — | 1.0 | — | — | — |
| | Sodium chloride | 0.6 | 0.6 | 0.6 | 0.6 | 0.6 | 0.6 | 0.6 | 0.6 | 0.6 | 0.6 | 0.6 |
| | Potassium hydroxide | 0.03 | 0.6 | 0.25 | 0.15 | 0.11 | 0.85 | — | 0.55 | 0.2 | — | — |
| | Hydrochloric acid | — | — | — | — | — | — | 0.3 | — | — | 0.6 | 1.9 |
| | Ethanol | 0.75 | 0.75 | 0.75 | 0.75 | 0.75 | 0.75 | 0.75 | 0.75 | 0.75 | 0.75 | 0.75 |
| | Perfume | 0.5 | 0.5 | 0.5 | 0.5 | 0.5 | 0.5 | 0.5 | 0.5 | 0.5 | 0.5 | 0.5 |
| | Water | # | # | # | # | # | # | # | # | # | # | # |
| | Total | 100 | 100 | 100 | 100 | 100 | 100 | 100 | 100 | 100 | 100 | 100 |
| | pH | 3.9 | 3.9 | 3.9 | 3.9 | 3.9 | 3.9 | 3.9 | 5.5 | 4.5 | 3.0 | 2.5 |

: Balance
(*1): Diapon K-TS, manufactured by Nippon Oil Corporation
(*2)POIZ C-150L, manufactured by Kao Corporation
(*3): SOFCARE KG-101W-E manufactured by Kao Corporation
(*4): Soft cat polymer SL-30 manufactured by Dow Chemical Company
(*5): Kao SOFCARE GP-1, manufactured by Kao Corporation
(*6): EMULGEN 103 manufactured by Kao Corporation
(*7): Adeka Carpol DL-30, manufactured by Adeka Corporation
(*8): AMPHITOL 20HD manufactured by Kao Corporation
(*9): AMPHITOL 20AB manufactured by Kao Corporation

TABLE 2

| Second composition | Hair cosmetic composition B(% by mass) | | | | | | | |
|---|---|---|---|---|---|---|---|---|
| | B1 | B2 | B3* | B4 | B5 | B6 | B7 | B8 |
| (A) Succinic acid | 1.5 | — | 1.5 | — | — | — | 1.5 | 1.5 |
| Malic acid | — | — | — | 1.5 | — | — | — | — |
| Lactic acid | — | — | — | — | 1.5 | — | — | — |
| Mandelic acid | — | — | — | — | — | 1.5 | — | — |
| Phenyl lactic acid | — | — | — | — | — | — | — | — |
| (C) p-Toluene sulfonic acid | 2.0 | 2.0 | — | 2.0 | 2.0 | 2.0 | 2.0 | 2.0 |
| β-Naphthalenesulfonic acid Na | 1.0 | 1.0 | — | 1.0 | 1.0 | 1.0 | 1.0 | 1.0 |
| Xylene sulfonic acid Na | — | — | — | — | — | — | — | — |
| (E) Laureth-16 | 0.2 | 0.2 | 0.2 | 0.2 | 0.2 | 0.2 | 0.2 | 0.2 |
| Ceteareth-7 | — | — | — | — | — | — | — | — |
| Ceteareth-25 | — | — | — | — | — | — | — | — |
| Polyglycerin-3 | — | — | — | — | — | — | — | — |
| Sorbitan oleate (*10) | — | — | — | — | — | — | — | — |
| PPG-3 Caprylyl ether | — | — | — | — | — | — | — | — |
| (G) Benzyl alcohol | 2.0 | 2.0 | 2.0 | 2.0 | 2.0 | 2.0 | 2.0 | 2.0 |
| Phenoxyethanol | — | — | — | — | — | — | — | — |
| (H) Cetrimonium chloride (*11) | — | — | — | — | — | — | 1.0 | 2.0 |
| Behentrimonium chloride | — | — | — | — | — | — | — | — |
| (I) Stearyl alcohol (*12) | — | — | — | — | — | — | — | — |
| Cetanol (*13) | — | — | — | — | — | — | — | — |
| Hydroxyethyl cellulose (*14) | 1.6 | 1.6 | 1.6 | 1.6 | 1.6 | 1.6 | 1.6 | 1.6 |
| DPG | 20.0 | 20.0 | 20.0 | 20.0 | 20.0 | 20.0 | 20.0 | 20.0 |
| PEG-45M (*15) | 0.1 | 0.1 | 0.1 | 0.1 | 0.1 | 0.1 | 0.1 | 0.1 |
| Amodimethicone (*16) | — | — | — | — | — | — | — | — |
| Ethanol | — | — | — | — | — | — | — | — |
| Potassium hydroxide | 1.8 | 0.6 | 1.2 | 1.7 | 1.5 | 1.1 | 1.8 | 1.8 |
| Perfume | 0.1 | 0.1 | 0.1 | 0.1 | 0.1 | 0.1 | 0.1 | 0.1 |
| Water | # | # | # | # | # | # | # | # |
| Total | 100 | 100 | 100 | 100 | 100 | 100 | 100 | 100 |
| (H)/(C) | 0 | 0 | 0 | 0 | 0 | 0 | 0.33 | 0.67 |
| pH | 6.0 | 6.0 | 6.0 | 6.0 | 6.0 | 6.0 | 6.0 | 6.0 |

| Second composition | Hair cosmetic composition B(% by mass) | | | | | | |
|---|---|---|---|---|---|---|---|
| | B9* | B10 | B11 | B12 | B13 | B14 | B15 |
| (A) Succinic acid | 1.5 | 5.0 | 5.0 | 3.0 | 2.5 | 0.8 | 0.3 |
| Malic acid | — | — | — | — | — | — | — |
| Lactic acid | — | — | — | — | — | — | — |
| Mandelic acid | — | — | — | — | — | — | — |
| Phenyl lactic acid | — | — | — | 1.0 | — | — | — |
| (C) p-Toluene sulfonic acid | 2.0 | 0.1 | 15.0 | 8.0 | 4.0 | 2.5 | 1.0 |
| β-Naphthalenesulfonic acid Na | 1.0 | — | — | — | — | — | — |
| Xylene sulfonic acid Na | — | — | — | 2.0 | — | — | — |
| (E) Laureth-16 | 0.2 | 0.2 | 0.2 | 0.01 | 0.1 | 1.24 | 9.0 |
| Ceteareth-7 | — | — | — | — | — | 0.3 | — |
| Ceteareth-25 | — | — | — | — | — | 0.06 | — |
| Polyglycerin-3 | — | — | — | — | — | 0.4 | — |
| Sorbitan oleate (*10) | — | — | — | — | — | — | 0.5 |
| PPG-3 Caprylyl ether | — | — | — | — | — | — | 0.5 |
| (G) Benzyl alcohol | 2.0 | 10.0 | 0.1 | 0.5 | 1.0 | 3.0 | 4.0 |
| Phenoxyethanol | — | — | — | — | — | — | 1.0 |
| (H) Cetrimonium chloride (*11) | 3.0 | — | — | — | — | — | — |
| Behentrimonium chloride | — | — | — | 0.5 | — | — | — |
| (I) Stearyl alcohol (*12) | — | — | — | 10.0 | 9.0 | 5.0 | 0.5 |
| Cetanol (*13) | — | — | — | 5.0 | — | — | — |
| Hydroxyethyl cellulose (*14) | 1.6 | 1.6 | 1.6 | 1.6 | 1.6 | 1.6 | 1.6 |
| DPG | 20.0 | 20.0 | 20.0 | 20.0 | 20.0 | 20.0 | 20.0 |
| PEG-45M (*15) | 0.1 | 0.1 | 0.1 | 0.1 | 0.1 | 0.1 | 0.1 |
| Amodimethicone (*16) | — | — | — | — | — | 1.5 | — |
| Ethanol | — | — | — | 0.3 | — | — | — |
| Potassium hydroxide | 1.8 | 4.2 | 8.2 | 2.8 | 2.5 | 1.5 | 0.6 |
| Perfume | 0.1 | 0.1 | 0.1 | 0.1 | 0.1 | 0.1 | 0.1 |
| Water | # | # | # | # | # | # | # |
| Total | 100 | 100 | 100 | 100 | 100 | 100 | 100 |
| (H)/(C) | 1.0 | 0 | 0 | 0.05 | 0 | 0 | 0 |
| pH | 6.0 | 6.0 | 6.0 | 4.0 | 5.0 | 6.5 | 7.0 |

*Not corresponds to the second composition
: Balance

*10: RHEODOL AO-10V, manufactured by Kao Corporation
*11: QUARTAMIN 60 W, manufactured by Kao Corporation
*12: KALCOL 8098 manufactured by Kao Corporation
*13: KALCOL 6098 manufactured by Kao Corporation
*14: HEC DAICEL SE-850K manufactured by Daicel Fine-Chem Ltd.
*15: Polyox WSR N-60K manufactured by Dow Chemical Company
*16: Silicone XS65-C0032 manufactured by Momentive Performance Materials Japan, Inc.

TABLE 3

| Third composition | | Hair cosmetics composition C (% by mass) C1 |
|---|---|---|
| (A) | Lactic-acid | 1.6 |
|  | Malic acid | 0.1 |
| (H) | Stearoxypropyl dimethylamine | 2.8 |
| (I) | Stearyl alcohol (*12) | 8.0 |
| (G) | Benzyl Alcohol | 0.2 |
|  | Hydroxyethyl cellulose (*14) | 0.1 |
|  | DPG | 2.6 |
|  | PEG-45M (*15) | 0.05 |
|  | Dimethicone (*17) | 4.5 |
|  | Amodimethicone (*16) | 0.3 |
|  | Perfume | 0.4 |
|  | Water | Balance |
|  | Total | 100 |
|  | pH | 3.4 |

*17: Mixture of dimethicone having a weight average molecular weight of about 200,000: about 50,000: about 650=93:140:67 (weight ratio)

(Preparation of Hair Tresses for Pretreatment Evaluation)

Hair tresses of 50 hairs 25 cm long were prepared using Japanese curly hair with no history of chemical treatment. The tresses was dipped in a 20-fold diluted aqueous solution of shampoo of the following formulation for 1 minute and rinsed with ion-exchanged water for 10 seconds. Next, the tress was dipped in a 20-fold diluted aqueous solution of a hair conditioner having the following formulation for 1 minute, rinsed with ion-exchanged water for 10 seconds, then towel-dried, and dried with a dryer (TESCOM, Inc., Nobby TNB1903, hot air) for 20 seconds. This was referred to as "hair tress for pre-treatment evaluation"

Formulation of Shampoos (pH7.0) ($ by Mass)

| Sodium Polyoxyethylene (2.5) Lauryl Ether Sulfate | 15.5 |
|---|---|
| Diethanolamide Ialolate | 2.3 |
| Edetate disodium | 0.15 |
| Sodium benzoate | 0.5 |
| Sodium chloride | 0.8 |
| Phosphoric acid | q.s. |
| Perfume, methylparaben | trace |
| Water | balance |
| Total | 100 |

Formulation of Hair Conditioners (pH4.4) (% by Mass)

| Stearoxypropyl dimethylamine | 0.8 |
|---|---|
| Stearyl alcohol | 3.1 |
| Lactic acid | 0.2 |
| Water | balance |
| Total | 100 |

(Treatment of Hair Tress for Pre-Treatment Evaluation)

Each hair tress was treated and evaluated according to the following method. All of the hair cleansing composition and the hair cosmetic composition were diluted 20 times with ion-exchanged water, and the bundle was dipped in each aqueous solution in an infinite bath at the time of treatment.

Example 1

The hair tress for pre-treatment evaluation was dipped in a 20-fold diluted aqueous solution of the hair cleansing composition A for 1 minute, and then rinsed with ion exchange water for 10 seconds. Then, the tress was dipped in a 20-fold diluted aqueous solution of hair cosmetic composition B for 6 minutes, rinsed with ion-exchanged water for 10 seconds, then towel-dried, and dried with a dryer for 20 seconds.

Example 2

The hair tress for pre-treatment evaluation was dipped in a 20-fold diluted aqueous solution of the hair cleansing composition A for 1 minute, and then rinsed with ion exchange water for 10 seconds. Next, the bundle was dipped in the 20-fold diluted aqueous solution of the hair cosmetic composition B for 6 minutes, and the tress was dipped in the 20-fold diluted aqueous solution of the hair cosmetic composition C without rinsing for 5 minutes, followed by rinsing with ion exchange water for 10 seconds, towel drying, and drying with a dryer for 20 seconds.

Example 3

In Example 2, the same process as in Example 2 was performed except that the tress was dipped in the 20-fold diluted aqueous solution of the hair cosmetic composition B for 6 minutes, followed by rinsing with ion exchange water for 10 seconds, and then dipped in the 20-fold diluted aqueous solution of the hair cosmetic composition C for 5 minutes.

Examples 4 to 16

The same process as in Example 1 was performed.

Comparative Examples 1 and 5

The hair tress for pre-treatment evaluation was dipped in a 20-fold diluted aqueous solution of the hair cleansing composition A for 1 minute, and then rinsed with ion exchange water for 10 seconds. Towel-dried and dried in a dryer for 20 seconds.

Comparative Example 2

The hair tress for pre-treatment evaluation was dipped in a 20-fold diluted aqueous solution of hair cosmetic composition B for 6 minutes, and then rinsed with ion exchange water for 10 seconds. Towel-dried and dried in a dryer for 20 seconds.

Comparative Examples 3, 4, and 6

The same process as in Example 1 was performed.

Evaluation Method

<Hair Tress Setting after Drying>

For the hair tress for pre-treatment evaluation and the evaluation hair tress after performing each treatment four times, the lateral width of the portion 15 cm from the root was measured, and the integration rate was calculated according to the following formula, and is shown in Tables 4 and 5. The higher the setting ratio, the higher the setting of the hair bundle.

$$\text{Setting rate (\%)} = \frac{\text{Width of the pretreated tress (cm)} - \text{width of the post-treated tress (cm)}}{\text{Width of the pretreatment hair tress (cm)}} \times 100 \quad \text{[Equation 1]}$$

<Stress Relaxation Rate of Dry Hair (20° C., 65% RH)>

One hair was cut out at random from each of the hair tress for pre-treatment evaluation and the evaluation hair tress after each of the five treatments. Using press assemblies (Dia-stron) for the FBS900 of fiber and hair bending systems (Dia-stron), excess hair was cut off by sandwiching the root side of the hair on a plastics tab (Dia-stron) so that the length of the hair exiting the tab was 5 mm. Thereafter, the pre-treatment evaluation hair and the post-5-time treatment evaluation hair were wetted with ion exchange water and then naturally dried at 20° C. and 65% RH for 24 hours.

The state hair was bent to a strain of 0.2 mm at 2.75 mm from the tip of the hair using a fiber and hair bending FBS900 and held for 3 minutes. The initial stress value and the stress value after 3 minutes were measured, and the bending stress relaxation rate was calculated according to the following equation. This same evaluation was performed a total of 5 times, and the average values are shown in Tables 4 and 5.

The higher the stress relaxation rate, the weaker the force to return to the original shape with respect to the external force of bending, and the higher the shapeability, i.e., plastic deformability.

$$\text{Percentage of stress relaxation (\%)} = \frac{\text{Initial stress value (mg)} - \text{stress value after 3 minutes (mg)}}{\text{Initial stress value (mg)}} \times 100 \quad \text{[Equation 2]}$$

<Formability when Stress is Applied to Dry Hair (20° C., 65% RH)>

One hair was cut out at random from each of the hair tress for pre-treatment evaluation and the evaluation hair tress after each of the five treatments. Mending tapes (made by Scotch Co.) with a 1.2 cm wide were placed between the roots of the cut hair to make a fixed part. The mending tape and hair were fixed using AronAlpha (registered trademark) (manufactured by Toa Synthesis Co.). Thereafter, the hair for evaluation before treatment and the hair for evaluation after 5 treatments were wetted with ion-exchanged water, dried while shaking for 30 seconds, and then suspended at 20° C. and 65% RH, and allowed to naturally dry for 24 hours.

The curl radius of a portion from the fixed portion on the root side of the humidified hair to 3.0 cm in the direction of the tip of the hair was measured. Next, similarly to the fixing portion on the root side, the fixing portion was also produced on the hair tip side, so that the hair between the fixing portions was 3.0 cm. Thereafter, the hair was stretched by 1% using a tensilonic TG-500N (manufactured by Minebea) and a load cell type TT3D-10N (manufactured by Minebea) and held for 3 minutes. Next, the fixed portion on the bristle tip side was cut off, and the curl radius of the portion from the fixed portion on the root side to the bristle tip 3.0 cm was measured. From the curl radius before and after stretching, the curl radius ratio was calculated according to the following equation. This same evaluation was performed a total of 5 times, and the average values are shown in Tables 4 and 5.

The higher the curl radius ratio, the greater the formability.

$$\text{Curl radius ratio} = \frac{\text{Curl radius after stretching (cm)}}{\text{Curl radius before stretching (cm)}} \quad \text{[Equation 3]}$$

<Smoothness of Hair Tresses after Drying>

The "smoothness" of the hair tress for evaluation after four treatments described above when touched by hand on the surface of the hair tress after drying was evaluated by 5 specialist panelists according to the following criteria, and an average point was calculated.

5: Smooth
4: Slightly smooth
3: Even
2: Slightly less smooth
1: Not smooth

<Appearance of the Second Composition>

Following the preparation of the second composition of the composition shown in Table 2, the appearance when the composition was left to stand at 25° C. for 24 hours was evaluated according to the following criteria.

3: Transparent
2: White turbidity
1: Separating

TABLE 4

| | | EXAMPLES | | | | | | | |
|---|---|---|---|---|---|---|---|---|---|
| | | 1 | 2 | 3 | 4 | 5 | 6 | 7 | 8 |
| Composition used | First composition (hair detergent A) | A1 | A1 | A1 | A2 | A1 | A3 | A4 | A5 |
| | Second composition (hair cosmetic B) * B3 does not fall under the second composition | B1 | B1 | B1 | B1 | B2 | B4 | B5 | B6 |

TABLE 4-continued

|  |  |  |  |  |  |  |  |  |  |
|---|---|---|---|---|---|---|---|---|---|
|  | Third composition (hair cosmetic C) | — | C1 | C1 | — | — | — | — | — |
| Procedure (from top to bottom) |  | Dipping in A1 (1 min) Rinsing Dipping in B1 (6 min) Rinsing — — Towel drying Dryer Drying | Dipping in A1 (1 min) Rinsing Dipping in B1 (6 min) — Dipping in C1 (5 min) Rinsing Towel drying Dryer Drying | Dipping in A1 (1 min) Rinsing Dipping in B1 (6 min) Rinsing Dipping in C1 (5 min) Rinsing Towel drying Dryer Drying | Dipping in A2 (1 min) Rinsing Dipping in B1 (6 min) Rinsing — — Towel drying Dryer Drying | Dipping in A1 (1 min) Rinsing Dipping in B2 (6 min) Rinsing — — Towel drying Dryer Drying | Dipping in A3 (1 min) Rinsing Dipping in B4 (6 min) Rinsing — — Towel drying Dryer Drying | Dipping in A4 (1 min) Rinsing Dipping in B5 (6 min) Rinsing — — Towel drying Dryer Drying | Dipping in A5 (1 min) Rinsing Dipping in B6 (6 min) Rinsing — — Towel drying Dryer Drying |
| Results of the evaluations | Percentage setting of hair tress after drying (%) | 35.2 | 43.3 | 39.4 | 32.0 | 25.8 | 30.9 | 21.1 | 19.8 |
|  | Stress relaxation rate (%) of dry hair | 26.3 | 27.0 | 26.5 | 24.7 | 25.5 | 27.2 | 27.1 | 26.4 |
|  | Formability when stressed on dry hair | 1.53 | 1.50 | 1.47 | 1.50 | 1.38 | 1.41 | 1.38 | 1.21 |
|  | Smoothness of hair tress after drying | 2.6 | 4.8 | 4.6 | 1.8 | 2.0 | 2.8 | 2.6 | 2.8 |

|  |  | Comparative example | | | | | Untreated |
|---|---|---|---|---|---|---|---|
|  |  | 1 | 2 | 3 | 4 | 5 |  |
| Composition used | First composition (hair detergent A) | A1 | — | A1 | A2 | A2 | — |
|  | Second composition (hair cosmetic B) * B3 does not fall under the second composition | — | B1 | B3* | B3* | — | — |
|  | Third composition (hair cosmetic C) | — | — | — | — | — | — |
| Procedure (from top to bottom) |  | Dipping in A1 (1 min) Rinsing — — Towel drying Dryer Drying | — Dipping in B1 (6 min) Rinsing Towel drying Dryer Drying | Dipping in A1 (1 min) Rinsing Dipping in B3 (6 min) Rinsing Towel drying Dryer Drying | Dipping in A2 (1 min) Rinsing Dipping in B3 (6 min) Rinsing Towel drying Dryer Drying | Dipping in A2 (1 min) Rinsing — — Towel drying Dryer Drying | — |
| Results of the evaluations | Percentage setting of hair tress after drying (%) | 0 | 0 | 4.3 | 0.7 | 2.8 | 0 |
|  | Stress relaxation rate (%) of dry hair | 21.9 | 22.3 | 19.8 | 23.9 | 23.2 | 18.7 |
|  | Formability when stressed on dry hair | 1.10 | 1.13 | 1.17 | 1.12 | 1.15 | 1.06 |
|  | Smoothness of hair tress after drying | 2.6 | 3.4 | 2.6 | 2.4 | 2.6 | 1 |

TABLE 5

|  |  | EXAMPLES | | | Comparative example |
|---|---|---|---|---|---|
|  |  | 1 | 9 | 10 | 6 |
| Composition used | First composition (hair detergent A) | A1 | A1 | A1 | A1 |
|  | Second composition (hair cosmetic B) *B9 does not correspond to the second composition | B1 | B7 | B8 | B9* |
| Procedure (from top to bottom) |  | Dipping in A1 (1 min) | Dipping in A1 (1 min) | Dipping in A1 (1 min) | Dipping in A1 (1 min) |

TABLE 5-continued

|  |  | EXAMPLES | | | Comparative example |
|---|---|---|---|---|---|
|  |  | 1 | 9 | 10 | 6 |
|  |  | Rinsing Dipping in B1 (6 min) Rinsing Towel drying Dryer Drying | Rinsing Dipping in B7 (6 min) Rinsing Towel drying Dryer Drying | Rinsing Dipping in B8 (6 min) Rinsing Towel drying Dryer Drying | Rinsing Dipping in B9 (6 min) Rinsing Towel drying Dryer Drying |
| Results of the evaluations | Percentage setting of hair tress after drying (%) | 35.2 | 35.6 | 28.8 | 6.3 |
|  | Stress relaxation rate (%) of dry hair | 26.3 | 26.2 | 24.2 | 23.2 |
|  | Formability when stressed on dry hair | 1.53 | 1.50 | 1.36 | 1.14 |
|  | Smoothness of hair tress after drying | 2.6 | 2.8 | 2.8 | 2.6 |
|  | Appearance of the second composition | 3 | 3 | 3 | 1 |

TABLE 6

|  |  | EXAMPLES | | | | | |
|---|---|---|---|---|---|---|---|
|  |  | 11 | 12 | 13 | 14 | 15 | 16 |
| Composition used | First composition (hair detergent A) | A6 | A7 | A8 | A9 | A10 | A11 |
|  | Second composition (hair cosmetic B) | B10 | B11 | B12 | B13 | B14 | B15 |
| Procedure (from top to bottom) |  | Dipping in A6 (1 min) Rinsing Dipping in B10 (6 min) Rinsing Towel drying Dryer Drying | Dipping in A7 (1 min) Rinsing Dipping in B11 (6 min) Rinsing Towel drying Dryer Drying | Dipping in A8 (1 min) Rinsing Dipping in B12 (6 min) Rinsing Towel drying Dryer Drying | Dipping in A9 (1 min) Rinsing Dipping in B13 (6 min) Rinsing Towel drying Dryer Drying | Dipping in A10 (1 min) Rinsing Dipping in B14 (6 min) Rinsing Towel drying Dryer Drying | Dipping in A11 (1 min) Rinsing Dipping in B15 (6 min) Rinsing Towel drying Dryer Drying |
| Results of the evaluations | Percentage setting of hair tress after drying (%) | 22.9 | 18.4 | 28.1 | 20.3 | 34.2 | 29.3 |
|  | Stress relaxation rate (%) of dry hair | 27.5 | 27.7 | 25.7 | 30.2 | 30.0 | 30.1 |
|  | Formability when stressed on dry hair | 1.46 | 1.47 | 1.53 | 1.51 | 1.50 | 1.43 |
|  | Smoothness of hair tress after drying | 3.4 | 3.8 | 3.4 | 3.5 | 3.4 | 2.6 |

From the results shown in Tables 4 and 6, the post-processing evaluation hair bundles of Examples 1 to 8 and 11 to 16 were superior to the post-processing evaluation hair tress of Comparative Examples 1 to 5 in the balance of the respective effects of the setting of the hair tress after drying, the stress relaxation rate of the dry hair, that is, the plastic deformability, the formability when stress was applied to the dry hair, and the smoothness of the dry hair tress.

From the results shown in Table 5, the post-processing evaluation hair tresses of Examples 1, 9, and 10 were superior to the post-processing evaluation hair tresses of Comparative Example 6 in the balance of the respective effects of the setting of the hair bundles after drying, the stress relaxation rate of the dry hair, that is, the plastic deformability, and the formability when stress was applied to the dry hair. Further, the second compositions used in Examples 1, 9 and 10 were transparent and excellent in stability without separation as compared with the second compositions used in Comparative Example 6.

The invention claimed is:

1. A hair treatment method comprising:
   (i): applying and rinsing off a first composition comprising component (A) and component (B) to hair; and
   (ii): after (i), applying to the hair a second composition comprising component (C) and component (H) and having a weight ratio (H)/(C) of component (H) to component (C) of less than 1;
   wherein:
   component (A) is a carboxylic acid having an inorganic value of 230 or more and 450 or less and an organic value of 50 or more and 250 or less, or a salt of the carboxylic acid;
   component (B) is an anionic surfactant;
   component (C) is an aromatic sulfonic acid hawing a molecular weight of 300 or less or a salt thereof; and
   component (H) is a cationic surfactant.

2. The hair treatment method of claim 1, further comprising rinsing the second composition on the hair after (ii), followed by applying a further composition to the hair.

3. The hair treatment method of claim 1, further comprising (iii) after (ii):
   (iii): applying to the hair a third composition comprising a cationic surfactant and a higher alcohol.

4. The hair treatment method of claim 3, further comprising rinsing off the second composition on the hair after (ii) and prior to (iii).

5. The hair treatment method of claim 3, wherein the second composition on the hair is not rinsed off after (ii) and prior to (iii).

6. The hair treatment method of claim 3, further comprising rinsing off the third composition on the hair after (iii).

7. The hair treatment method according to claim 1, wherein the content of the component (A) in the first composition is 0.1% by mass or more and 5% by mass or less.

8. The hair treatment method according to claim 1, wherein the pH at 25° C. when the first composition is diluted 20 times with water is 2.0 or more and 7.0 or less.

9. The hair treatment method according to claim 1, wherein the content of the component (C) in the second composition is 0.1% by mass or more and 15% by mass or less.

10. The hair treatment method according to claim 1, wherein the content of the cationic surfactant in the second composition is less than 6.0% by mass.

11. The hair treatment method according to claim 1, wherein the second composition further comprises component (A).

* * * * *